United States Patent [19]

Murchison et al.

[11] 4,199,522

[45] Apr. 22, 1980

[54] PROCESS FOR PRODUCING OLEFINS FROM CARBON MONOXIDE AND HYDROGEN

[75] Inventors: Craig B. Murchison, Midland; Dewey A. Murdick, Hope, both of Mich.

[73] Assignee: The Dow Chemical Company, Midland, Mich.

[21] Appl. No.: 944,228

[22] Filed: Sep. 20, 1978

Related U.S. Application Data

[63] Continuation-in-part of Ser. No. 814,760, Jul. 11, 1977, abandoned.

[51] Int. Cl.$^2$ ............................................ C07C 1/04
[52] U.S. Cl. .................... 260/449 R; 260/449 M; 260/449.6 R; 260/449.6 M; 252/439; 252/447; 252/465; 252/466 PT; 252/466 J; 252/468; 252/473
[58] Field of Search ............... 260/449 R, 449.6 R, 260/449 M, 449.6 M

[56] References Cited

U.S. PATENT DOCUMENTS

| | | | |
|---|---|---|---|
| 2,284,468 | 5/1942 | Burk et al. | 260/449.6 |
| 2,490,488 | 12/1949 | Stewart | 260/449 R |
| 2,960,518 | 11/1960 | Peters | 260/449.6 |
| 2,973,384 | 2/1961 | Hayoshi et al. | 260/449.6 |
| 3,240,698 | 3/1966 | Leak et al. | 260/449 R |
| 3,842,113 | 10/1974 | Ichikawa et al. | 260/449 R |
| 3,842,121 | 10/1974 | Ichikawa et al. | 260/449 R |
| 3,941,819 | 3/1976 | Vannice et al. | 260/449 R |

FOREIGN PATENT DOCUMENTS

593940 10/1947 United Kingdom .................. 260/499.6

OTHER PUBLICATIONS

Schultz et al., Noble Metal, Molybdenum and Tungsten in Hydrocarbon Synthesis Repot of Investigators, No. 697x, Bur. of Mins, 1967, pp. 1-19.

Mills et al., Catalysis Reviews, Marcell Dekker, New York, 1974, vol. 8, pp. 160-209.

Primary Examiner—Howard T. Mars
Attorney, Agent, or Firm—G. R. Plotecher

[57] ABSTRACT

Olefins of two to four carbon atoms are prepared by an improved Fischer-Tropsch process, the improvement comprising the use of a catalyst having a surface area less than about 100 m$^2$/g and consisting essentially of:
(1) at least one material selected from the group consisting of the sulfide, oxide or metal of Mo, W, Re, Ru, Ni, Pd, Rh, Os, Ir and Pt;
(2) at least one material selected from the group consisting of the hydroxide, oxicde or salt of Li, Na, K, Rb, Cs, Mg, Ca, Sr, Ba and Th; and
(3) optionally, a support.

29 Claims, No Drawings

PROCESS FOR PRODUCING OLEFINS FROM CARBON MONOXIDE AND HYDROGEN

CROSS-REFERENCE TO RELATED APPLICATION

This is a continuation-in-part of application Ser. No. 814,760, filed July 11, 1977 abandoned.

BACKGROUND OF THE INVENTION

1. Field of the Invention

This invention relates to an improved Fischer-Tropsch process for the production of olefinic $C_2$–$C_4$ hydrocarbons.

2. Description of the Prior Art

The art contains many examples of metals known to be useful in reacting carbon monoxide with hydrogen to produce a variety of compounds—both hydrocarbons and oxygenated compounds. These metals include, among others, Mo, W, Th, Ru, Re, Pd, Ni, Co, and Fe. It is upon the last two of these metals that most commercial experience is based. In what has come to be called the Fischer-Tropsch Synthesis, carbon monoxide and hydrogen are reacted over an iron or cobalt catalyst to produce saturated and unsaturated hydrocarbons and oxygenated compounds containing from one to as many as one thousand carbon atoms. The hydrocarbons can be aliphatic, alicyclic, or aromatic. Commercial utilization of this synthesis prior to 1950 was accomplished largely in Germany and is summarized in Storch, Columbic, and Anderson: *The Fisher-Tropsch and Related Synthesis*, John Wiley and Sons, New York 1951.

The major disadvantages in the prior art processes and catalysts is that most of them are not capable of selectively producing olefins. A process capable of producing olefins of low molecular weight could be used as a source of feedstock for a variety of petrochemical plants.

SUMMARY OF THE INVENTION

According to this invention, the process of producing hydrocarbons from contacting carbon monoxide and hydrogen at reactive conditions is improved by increasing the yield of olefinic hydrocarbons containing from 2 to 4 carbon atoms by contacting the carbon monoxide and hydrogen with a catalyst having a surface area less than about 100 $m^2/g$ and consisting essentially of:

(A) between about 1 percent and about 95 percent by weight based upon the weight of the catalyst of at least one material selected from the group consisting of the sulfide, oxide or metal of molybdenum, tungsten, rhenium, ruthenium, nickel, palladium, rhodium, osimium, iridium and platinum; and (B) between about 0.05 percent and about 50 percent by weight based upon the weight of the catalyst of at least one material selected from the group consisting of the hydroxide, oxide or salt of lithium, sodium, potassium, rubidium, cesium, magnesium, calcium, strontium, barium and thorium.

Optionally, the catalyst can contain as a third component a support. This invention markedly increases the production of $C_2$–$C_4$ olefins, particularly $C_3$ and $C_4$ olefins.

DETAILED DESCRIPTION OF THE PREFERRED EMBODIMENTS

The carbon monoxide required for the process can be obtained from any carbon source, such as from the degradation of coal or of high molecular weight hydrocarbon residuals. The molar ratio of hydrogen to carbon monoxide ranges generally from at least about 0.25 and preferably about 0.5 to an upper limit of about 4 and preferably about 1.5.

Process reaction conditions can vary over a rather broad range. The pressure can vary from at least about 1 psig and preferably about 75 psig to an upper limit of about 1500 psig and preferably about 500 psig. The reaction temperature ranges from at least about 200° C. and preferably about 300° C. to an upper limit of about 600° C. and preferably about 400° C.

The catalyst is typically either a two- or a three-component system. The first component is at least one material selected from the group consisting of the sulfide, oxide or metal of molybdenum, tungsten, rhenium, ruthenium, nickel, palladium, rhodium, osmium, iridium and platinum. "At least one" means that the first component can consist of two or more members of this enumerated group, including such combinations as the sulfide, oxide and metal of one element, or the oxides or sulfides of different elements, or the sulfide of one element and the oxide of another, or different oxides or sulfides, if any, of the same element, etc. As used herein, "sulfide" includes those compounds that have oxygen and sulfur directly attached to the same metal atom, such as O-Mo-S. This first component is present in an amount, based upon the weight of the catalyst, of at least about 1 and preferably at least about 10 weight percent with an upper limit of about 95 and preferably about 50 weight percent. A preferred first component is at least one material selected from the group consisting of the sulfide, oxide or metal of molybdenum and tungsten. These molybdenum and tungsten materials exhibit exceptionally good sulfur tolerance. An especially preferred first component is at least one material selected from the group consisting of the sulfide, oxide or metal of molybdenum.

The second component is at least one material selected from the group consisting of the hydroxide, oxide or salt of lithium, sodium, potassium, rubidium, cesium, magnesium, calcium, strontium, barium and thorium. "At least one" means that the second component can consist of two or more members of this enumerated group, including such combinations as the hydroxide, oxide and salt of one element, or the hydroxides, oxides or salts of different elements, or the hydroxide of one element and the oxide of another, or different oxides or salts, if any, of the same element, etc. The second component is present in an amount, based upon the weight of the catalyst, of at least about 0.05 and preferably at least about 1 weight percent with an upper limit of about 50 and preferably about 10 weight percent. A preferred second component is at least one material selected from the group consisting of the hydroxide, oxide or salt of lithium, sodium, potassium, rubidium or cesium. An especially preferred second component is at least one material selected from the group consisting of the hydroxide, oxide or salt of potassium.

Obviously, the optional support is not necessary to this invention but one is often employed for reasons of convenience. Virtually any support can be used but those most typical are the many and varied forms of alumina and carbon, silica, zirconia, zircon (a mixture of zirconia and silica), titanium dioxide, magnesia or mixtures thereof. Other suitable supports can also be used.

An alumina support is preferred. Based upon the weight of the catalyst, the support can comprise between about 1 and preferably at least about 40 percent of the catalyst with an upper limit of about 98.95 percent. If a support is present, most preferably it comprises at least about 60 percent of the catalyst.

Components of the catalyst of this invention can be present per se, or as an integral part of one another or as a combination thereof. Illustrative of components being present as an integral part of one another, certain supports (where a support is present) contain relatively small (based on the weight of the support) amounts of alkali metal hydroxides and/or oxides.

Preferred species of the catalyst of this invention have as a first component at least one material selected from the group consisting of the sulfide, oxide or metal of molybdenum and tungsten. More preferred species have as a first component at least one material selected from the group consisting of the sulfide, oxide or metal of molybdenum and tungsten and as a second component at least one material selected from the group consisting of the hydroxide, oxide or salt of lithium, sodium, potassium, rubidium and cesium. Still more preferred species have as a first component at least one material selected from the group consisting of the sulfide, oxide or metal of molybdenum and tungsten, as a second component at least one material selected from the group consisting of the hydroxide, oxide or salt of lithium, sodium, potassium, rubidium and cesium, and as a third component an alumina, silica, carbon, zirconia, zircon or magnesium support. Especially preferred species have as a first component at least one material selected from the group consisting of the sulfide, oxide or metal of molybdenum, as a second component at least one material selected from the group consisting of the hydroxide, oxide or salt of potassium, and as a third component an alumina support.

It is theorized that the efficient production of olefins by the process of this invention is related to the surface area of the catalyst. Supported or unsupported, the more efficient catalysts useful in the process of the invention possess a surface area of less than about 100 square meters per gram (m$^2$/g) measured by the Brunauer, Emmett and Teller (BET) method and preferably less than about 40 m$^2$/g. The BET method is described by R. B. Anderson, *Experimental Methods in Catalytic Research*, p. 48–66 (Academic Press, 1968).

In one embodiment of this invention, the catalyst can be represented by the formulae:

$$Ma_xH_yMeO_3C_2O_4 \quad (I)$$

and $$MbMeO_3C_2O_4. \quad (II)$$

Ma is a metal selected from the group consisting of Li, Na, K, Rb, Cs, and mixtures thereof; Mb is a metal selected from the group consisting of Mg, Ca, Sr, Ba, Th, and mixtures thereof; Me is a metal selected from the group consisting of Mo and W; and x is 1 or 2 and y is 0 or 1 with the provisoes that when x is 1, y is 1 and when x is 2, y is 0. Catalysts of I are preferred to catalysts of II; catalysts wherein Ma is potassium are preferred to catalysts wherein Ma is Li, Na, Rb or Cs; and catalysts wherein Ma is potassium and Me is molybdenum are especially preferred. The catalyst species of this particular embodiment have a surface area less than about 100 m$^2$/g (generally less than about 40 m$^2$/g) and can be used either singly or in combination with one another.

The catalyst is generally prepared by dissolving two moles of oxalic acid per mole of oxide of Me in water, adding one mole of a hydrated MaMe oxide, adjusting the pH of the resulting solution to about 6, and allowing the solution to cool. Crystals of an ammonium complex of $Ma_xH_yMeO_3C_2O_4$ or $MbMeO_3C_2O_4$ form and precipitate from solution. The crystals are then reduced with hydrogen for a suitable period, e.g., about 24 hours, at a series of temperatures commencing with a minimum temperature of about 200° C. and culminating in a maximum temperature of about 600° C. After reduction, the crystals are immediately useful as a catalyst in the process of the invention as they require no third component.

The following examples should be considered illustrative of the surprising results obtainable with the invention and should not be construed as limiting of the invention. All percentages are by weight unless otherwise indicated.

SPECIFIC EMBODIMENTS

Apparatus and Procedure

In preparation of a supported catalyst, supports were impregnated by a technique known as the incipient wetness technique. Water-soluble salts of active components of the catalyst and a support were chosen. A quantity of water which a catalyst support will adsorb is known as its pore volume. According to the desired catalyst loading, a quantity of the soluble salts was dissolved in water approximately equal to the pore volume of the support. The support was then immersed in the water which it absorbed completely. A wet cake was formed. The wet cake was first air-dried at room temperature for sixteen to twenty-four hours. It was then placed in an oven and heated at a rate of between about 0.4° C. and about 1.8° C. per minute in the presence of air or nitrogen to a final temperature of between about 500° C. and about 650° C. The catalyst was held at this final temperature for about six hours before being allowed to cool slowly to room temperature.

In the examples, an apparatus was utilized which included a sequential order three high-pressure gas bottles, a manifold, and a reactor equipped on the downstream side with a fine metering valve and a rotameter through a sampling manifold to a gas chromatograph. One bottle contained a mixture of hydrogen and carbon monoxide in a one to one molar ratio. The second bottle contained a mixture of hydrogen and carbon monoxide in a one to two ratio. The third bottle contained hydrogen alone. Each bottle was independently connected to the manifold. The manifold was constructed such that any of the three bottles could be used to feed the reactor. Through the sampling manifold, the product of each reactor could be piped to the gas chromatograph for analysis.

Before each run, catalyst was loaded in the reactor to be used and heated to 350° C. over a four-hour period in the presence of hydrogen. The hydrogen flow and a temperature of 350° C. were maintained for sixteen more hours. Then the catalyst was raised to a final temperature over a four-hour period. The final temperature was between about 500° C. and about 650° C. This final temperature was held for about two to forty-eight hours. The outlet temperature of each reactor in use was maintained by the use of a hot air stream. The reactors were then lowered to operating temperature in the presence of hydrogen. Next, feed from the high-pressure gas bottle containing hydrogen and carbon monoxide was allowed to flow through the manifold to the reactor. Pressure, flow, and temperature were adjusted to operating values. Unless otherwise indicated the operating values were for the hourly space velocity: 300 hr$^{-1}$; for the temperature: 300° C.; and for the pressure: 300 psig. The $H_2/CO$ ratio was one unless otherwise indicated.

Subscripts, e.g., the 1 in $C_1$, etc., in all examples indicate the number of carbon atoms. All hydrocarbon analyses are reported in carbon mole percent in all examples. "Carbon mole percent" is defined as 100 times the moles of carbon present in a hydrocarbon fraction divided by the total moles of carbon in the product hydrocarbon. If one mole of ethylene is found in the $C_2$ fraction, this is counted as two moles of carbon. The term "product hydrocarbon" excludes any carbon dioxide produced. Unless otherwise indicated, molybdenum concentrations are reported as $MoO_3$ equivalents and potassium concentrations are reported as $K_2O$ equivalents. The surface area (support plus the first and second components) of each catalyst was less than about 40 $m^2/g$, unless indicated to the contrary.

EXAMPLE 1

In order to demonstrate the effect of increasing concentration of the second component of the catalyst, the following three runs were conducted.

The catalyst of the first run (1A) was commercially available and was composed of 10 weight percent $MoO_3$ on alumina. It is sold as Mo-0502T-⅛ by the Harshaw Chemical Company. In run 1B, the catalyst of Run 1A was modified by the addition of 2 weight percent $K_2O$ according to the incipient wetness technique described above. In run 1C, the catalyst was prepared by dissolving 93.2 g $Al(NO_3)_3 \cdot 9H_2O$, 15.1 g $(NH_4)_6Mo_7O_{24} \cdot 4H_2O$, and 3.6 g $KNO_3$ in 850 cc of water, evaporation of the water to form a wet cake, and drying the wet cake under reduced pressure for about 12 to 24 hours. The wet cake was then calcined by heating it in the presence of air from ambient temperature at 650° 1 C. at a rate of about 1.8° C. per minute and holding it at 650° C. for 6.5 hours. The catalyst was reduced to particles of about 1 mm diameter by grinding. On a weight basis, the calcined catalyst was composed of 48 percent $MoO_3$, 48 percent $Al_2O_3$ and 4 percent $K_2O$.

|  | Run 1A | Run 1B | Run 1C |
|---|---|---|---|
| Paraffins: |  |  |  |
| $C_1$ | 62.3 | 42.0 | 37.6 |
| $C_2$ | 21.6 | 31.3 | 25.8 |
| $C_3$ | 9.0 | 12.7 | 13.8 |
| $C_4$ | 3.9 | 6.6 | 4.4 |
| Olefins: |  |  |  |
| $C_2$ | 0.9 | 2.2 | 0.9 |
| $C_3$ | — | 2.7 | 8.7 |
| $C_4$ | — | 0.9 | 4.8 |
| Olefins & Paraffins: |  |  |  |
| $C_5$ | 2.3 | 1.5 | 2.1 |
| $C_6$ | — | — | 1.8 |
| Carbon Monoxide Conversion (mole percent) | 70.0 | 58.0 | 57.0 |
| Weight percent $K_2O$ | 0 | 2.0 | 4.0 |
| Percent Olefins in $C_2$-$C_4$ Fraction | 2.6 | 11.5 | 24.7 |
| BET Surface Area ($m^2/g$) | 64 | 64 | ~5 |

The results of Runs 1A, 1B, and 1C are summarized above. The poor yield of olefins in the desired $C_2$-$C_4$ range has been improved by the addition of 2 weight percent $K_2O$ to the catalyst of Run 1B. The best yield of olefins in the desired range is obtained in Run 1C.

EXAMPLE 2

In Run 2 the catalyst is that of Run 1C. However, in Run 2 the $H_2/CO$ ratio was decreased from 1 to ½. The results of Run 1C and Run 2 are summarized below for comparison.

|  | Run 1C | Run 2 |
|---|---|---|
| Paraffins: |  |  |
| $C_1$ | 37.6 | 24.6 |
| $C_2$ | 25.8 | 23.2 |
| $C_3$ | 13.8 | 15.3 |
| $C_4$ | 4.4 | 5.8 |
| Olefins: |  |  |
| $C_2$ | 0.9 | 4.2 |
| $C_3$ | 8.7 | 13.8 |
| $C_4$ | 4.8 | 8.0 |
| Olefins & Paraffins: |  |  |
| $C_5$ | 2.1 | 3.4 |
| $C_6$ | 1.8 | 1.7 |
| Carbon Monoxide Conversion (mole percent) | 57.0 | 37.0 |
| Weight percent $K_2O$ | 4.0 | 4.0 |
| $H_2/CO$ Ratio | 1:1 | 1:2 |
| Percent Olefins in $C_2$-$C_4$ Fraction | 24.7 | 37.0 |
| BET Surface Area ($m^2/g$) | ~5 | ~5 |

These data indicate that a decrease in the $H_2/CO$ ratio increases the yield of olefins in the desired $C_2$ to $C_4$ range at the expense of a drop in the CO conversion.

EXAMPLE 3

In Run 3, the catalyst was prepared as in Run 1C except that it was composed of 45 percent $MoO_3$, 45 percent $Al_2O_3$, and 10 percent $K_2O$. The results of both Run 1C and Run 3 are summarized below for comparison.

|  | Run 1C | Run 3 |
|---|---|---|
| Paraffins: |  |  |
| $C_1$ | 37.6 | 30.1 |
| $C_2$ | 25.8 | 4.5 |
| $C_3$ | 13.8 | 2.0 |
| $C_4$ | 4.4 | 1.2 |
| Olefins: |  |  |
| $C_2$ | 0.9 | 6.6 |
| $C_3$ | 8.7 | 6.0 |
| $C_4$ | 4.8 | 2.8 |
| Olefins & Paraffins: |  |  |
| $C_5$ | 2.1 | 0.3 |
| $C_6$ | 1.8 | 2.0 |
| Oil | — | 44.6 |
| Carbon Monoxide Conversion (mole percent) | 57.0 | 54.0 |
| Weight percent $K_2O$ | 4.0 | 10.0 |
| Percent Olefins in $C_2$-$C_4$ Fraction | 24.7 | 66.7 |
| BET Surface Area ($m^2/g$) | ~5 | 6.5 |

These data indicate that while an increase in concentration of the second component of this catalyst from 4 percent to 10 percent does not significantly improve the yield of $C_2$-$C_4$ olefins, it does significantly improve the percent of olefins in the $C_2$-$C_4$ hydrocarbon fraction. This increase in the concentration of the second component also changes the olefinic product distribution.

EXAMPLE 4

For Runs 4A and 4B a commercially available zircon, known as Carborundum ZLT and sold by the Carborundum Company, was impregnated via the incipient wetness technique with 10 percent $MoO_3$ to make the catalyst for Run 4A and with 10 percent $MoO_3$ and 5 percent $K_2O$ to make the catalyst for Run 4B. The hourly space velocity in Run 4A of 323 $hr^{-1}$ and the hourly space velocity of Run 4B was 362 $hr^{-1}$.

|  | Run 4A | Run 4B |
| --- | --- | --- |
| Paraffins: | | |
| $C_1$ | 62.4 | 19.1 |
| $C_2$ | 25.9 | 6.7 |
| $C_3$ | 7 | 5 |
| $C_4$ | 1.2 | 2.2 |
| Olefins: | | |
| $C_2$ | — | 1.7 |
| $C_3$ | — | 12.4 |
| $C_4$ | — | 9 |
| Olefins & Paraffins: | | |
| $C_5$ | — | 1.3 |
| $C_6$ | — | 1.7 |
| Oil | 3.4 | 40.8 |
| Carbon Monoxide Conversion (mole percent) | 60 | 92 |
| Weight percent $K_2O$ | 0 | 5.0 |
| Percent Olefin in $C_2$–$C_4$ Fraction | 0 | 65.0 |
| BET Surface Area* ($m^2/g$) | 0.31 | 0.31 |

*Surface area of support only.

These data indicate the dramatic improvement in yield of desired olefins effected by the second component of the catalyst. The presence in Run 4B of the two components, $MoO_3$ and $K_2O$, on a support of low surface area resulted in a high carbon monoxide conversion and a good olefin yield in the $C_2$–$C_4$ fraction.

EXAMPLE 5

In this run the incipient wetness technique was used to impregnate Carborundum ZRMT (93 percent $ZrO_2$, 5 percent CaO) which is sold by the Carborundum Company with 10 percent $MoO_3$ and 5 percent $K_2O$. Results are summarized below:

| Paraffins: | |
| --- | --- |
| $C_1$ | 37.3 |
| $C_2$ | 5.3 |
| $C_3$ | 3.3 |
| $C_4$ | 0.9 |
| Olefins: | |
| $C_2$ | 8.7 |
| $C_3$ | 5.4 |
| $C_4$ | 1.9 |
| Olefins & Paraffins: | |
| $C_5$ | — |
| $C_6$ & higher | 37.1 |
| Carbon Monoxide Conversion (mole percent) | 39.8 |
| Percent Olefin in $C_2$–$C_4$ Fraction | 62.7 |
| BET Surface Area* ($m^2/g$) | 0.16 |

*Surface area of support only.

These data indicate that a low surface area support impregnated with both components of the catalyst is effective to produce a major amount of olefins in the $C_2$ to $C_4$ fraction.

EXAMPLE 6

In this run a potassium oxalatomolybdate was prepared by dissolving with stirring 12.7 g (0.1 mole) of oxalic acid and 14.4 g (0.1 mole) of molybdenum trioxide in water to form a solution. After the addition of 12.6 g (0.1 mole) more of oxalic acid and 30.7 g (0.0937 mole) of $K_2MoO_4 \cdot 5H_2O$, a precipitate formed. The pH of the solution, measured at 2, was adjusted to 6 by the addition of a sufficient quantity of 28 percent ammonia. At this point the precipitate disappeared. The solution which had been heated by the addition of ammonia was allowed to cool. Crystals formed, were analyzed by x-ray fluorescence, and were found to contain 25.2 percent Mo, 23.4 percent K, and 5.7 percent C, with the remainder being hydrogen and oxygen. The crystals were dried, placed in a reactor, and hydrogen was passed through the reactor for about a 60-hour period during which time the temperature was raised in steps from 150° C. to 520° C. with the pressure remaining fixed at 15 psig.

| Results: | |
| --- | --- |
| Paraffins: | |
| $C_1$ | 23.8 |
| $C_2$ | 3.9 |
| $C_3$ | 1.4 |
| $C_4$ | 0.9 |
| Olefins: | |
| $C_2$ | 8.3 |
| $C_3$ | 9.5 |
| $C_4$ | 5.8 |
| Olefins & Paraffins: | |
| $C_5$ | — |
| $C_6$ & higher | 46.3 |
| Carbon Monoxide Conversion (mole percent) | 42.7 |
| Percent Olefin in $C_2$–$C_4$ Fraction | 79.2 |
| BET Surface Area ($m^2/g$) | 6.1 |

These data illustrate an unsupported catalyst useful in the process of the invention to improve the yield of olefins in the $C_2$ to $C_4$ range.

EXAMPLE 7

$Al_2O_3$ (105 g, manufactured by Carborundum under the designation SAEHS-33) was impregnated with a solution consisting of $MoO_3$ (41.5 g), ethylenediamine tetraacetic acid (42.6 g) and $K_2CO_3$ (8.12 g) dissolved in 500 ml of water with an adjusted (by $NH_4OH$) pH of about 6. The $Al_2O_3$ was impregnated by dripping the solution onto it while the $Al_2O_3$ was rotated within a heated (120° C.) drum. Three individual samples of the resulting catalyst were employed in the following runs:

|  | 7A | 7B | 7C |
| --- | --- | --- | --- |
| Temperature (°C.) | 396 | 396 | 422 |
| Pressure (psig) | 286 | 143 | 143 |
| HSV ($hr^{-1}$) | 536 | 447 | 422 |
| Paraffins: | | | |
| $C_1$ | 32.0 | 29.9 | 33.6 |
| $C_2$ | 5.4 | 4.1 | 5.3 |
| $C_3$ | 3.7 | 5.0 | 6.1 |
| $C_4$ | 1.3 | 1.2 | 1.4 |
| Olefins: | | | |
| $C_2$ | 9.2 | 11.0 | 11.2 |
| $C_3$ | 3.7 | 5.4 | 6.4 |
| $C_4$ | 2.1 | 2.2 | 2.4 |
| Olefin & Paraffin: | | | |
| $C_5$ & Highers | 41.3 | 41.1 | 33.7 |
| CO Conversion (mole percent) | 48.4 | 32.0 | 45.9 |
| Percent Olefin in $C_2$–$C_4$ Fraction | 59.0 | 64.0 | 61.0 |
| BET Surface Area* ($m^2/g$) | 4.0 | 4.0 | 4.0 |

*Surface area of support only.

A comparison of the 7A and 7B results demonstrate that a reduction of pressure increases the selectivity of $C_2$–$C_4$ olefins but at the expense of CO conversion. However, the results of 7C demonstrate that this increased selectivity can be maintained without substantial sacrifice of CO conversion by an increase in temperature.

EXAMPLE 8

To demonstrate the sulfur tolerance of certain catalyst species of this invention, particularly those comprising a sulfide, oxide or metal of molybdenum, a catalyst comprising 10 percent $MoO_3$, 2 percent $K_2O$ and 88 percent Carborundum SAEHS-33 $Al_2O_3$ was first exposed to the following conditions for 366 hours:

| | |
|---|---|
| Temperature (°C.) | 417 |
| Pressure (psig) | 287 |
| HSV ($hr^{-1}$) | 282 |
| $H_2$/CO | 0.94 |
| BET Surface Area* ($m^2$/g) | 4 |

*Surface area of support only.

After this first exposure, the catalyst was then exposed to an additional 116 hours of the same conditions except that 20 ppm $H_2S$ was added and the HSV increased to 356 $hr^{-1}$. The results of a gas phase analysis of both exposures are reported below:

| | Without $H_2S$ | With $H_2S$ |
|---|---|---|
| Paraffins: | | |
| $C_1$ | 39.8 | 43.0 |
| $C_2$ | 7.2 | 6.2 |
| $C_3$ | 8.4 | 2.2 |
| $C_4$ | 1.0 | 1.1 |
| Olefins: | | |
| $C_2$ | 22.7 | 19.8 |
| $C_3$ | 16.6 | 19.9 |
| $C_4$ | 4.3 | 6.9 |
| CO Conversion (mole percent) | 41.7 | 37.1 |

These data demonstrate no significant change in activity (CO conversion) or gas phase olefin selectivity upon exposure to a relatively large concentration of $H_2S$.

EXAMPLE 9 AND CONTROL

Two samples each of equal weight of catalyst Mo-1201 (surface area of 160 $m^2$/g), and Mo-0502 (surface area of 60 $m^2$/g), both 10 percent molybdenum trioxide on alumina and both manufactured by the Harshaw Chemical Company, were used as catalysts in these experiments. One sample of each catalyst was alkalized with potassium carbonate while the other sample of each catalyst was alkalized in a similar fashion plus sulfided with potassium sulfide, ammonium sulfide and molybdenum sulfide. All the catalysts were then reduced with hydrogen at 500° C. and subsequently used to catalyze a Fischer-Tropsch hydrocarbon synthesis. The parameters and results of these experiments are reported below:

| | Mo-1201 | Mo-0502 |
|---|---|---|
| Process parameters: | | |
| Catalyst surface area ($m^2$/g) | 160 | 60 |
| Pressure (psig) | 300 | 300 |
| $H_2$/CO Ratio | 0.8–1 | 0.8–1 |
| Temperature (°C.) | | |
| A. | 400 | 400 |
| B. | 370 | 370 |
| Process results: | | |
| (% hydrocarbon product) | | |
| A. Oxide form of catalyst | | |
| (10% $MoO_3$, 2% $K_2O$) | | |
| $C_1$ | 47 | 43 |
| $C_2$–$C_4$ (saturated) | 51 | 51 |
| $C_2$–$C_4$ (unsaturated) | 1 | 5 |
| $C_5$+ | 1 | 1 |
| Total | 100 | 100 |
| B. Sulfide form of catalyst | | |
| (15% $MoO_3$, 2.7% $K_2O$) | | |
| $C_1$ | 60 | 54 |
| $C_2$–$C_4$ (saturated) | 40 | 43 |
| $C_2$–$C_4$ (unsaturated) | 0 | 3 |
| $C_5$+ | 0 | 0 |
| Total | 100 | 100 |

The above data demonstrate the surprising effect that surface area has on the synthesis of $C_2$–$C_4$ olefinic hydrocarbons, specifically:

(a) The oxide form of catalyst Mo-1201 having a surface area of 160 $m^2$/g produced only 1 percent $C_2$–$C_4$ olefinic hydrocarbon and the sulfide form of the same catalyst produced no $C_2$–$C_4$ olefinic hydrocarbon; and (b) the oxide form of catalyst Mo-0502 having a surface area of 60 $m^2$/g produced 5 percent $C_2$–$C_4$ olefinic hydrocarbon and the sulfide form of the same catalyst produced 3 percent $C_2$–$C_4$ olefinic hydrocarbon.

EXAMPLE 10

An alumina support having a surface area of 2.6 $m^2$/g and manufactured by Carborundum Co. as SAHT-99 was impregnated by the incipient wetness technique with 30 percent $MoO_3$ and 4 percent $K_2O$. The process parameters and results are reported below.

| | |
|---|---|
| Process Parameters: | |
| Temperature (°C.) | 404 |
| Pressure (psig) | 485 |
| HSV ($hr^{-1}$) | 482 |
| $H_2$:Co (mole quotient) | 0.88 |
| Process Results: | |
| Paraffins | Selectivity (Carbon mole %) |
| $C_1$ | 24.2 |
| $C_2$ | 8.2 |
| $C_3$ | 5.9 |
| $C_4$ | 1.5 |
| Olefins | |
| $C_2$ | 8.7 |
| $C_3$ | 9.4 |
| $C_4$ | 4.1 |
| Olefins and Paraffins | |
| $C_5$ plus | 37.9 |
| CO Conversion (%) | 79 |

EXAMPLES 11–14

Catalysts were prepared from four different supports to demonstrate the wide variety of supports that can be optionally used in the practice of this invention. All catalysts were prepared by the incipient wetness technique. Catalyst compositions, process parameters and process results are tabulated below.

Catalyst Compositions

A. $MoO_3$—30%; $K_2O$—5%; Silicon-carbide support—65% (Carborundum Co. product CIIO analyzed as SiC—77.9%, $Al_2O_3$—5.5% and $SiO_2$—14.9% with a surface area of 0.3 $m^2$/g).

B. $MoO_3$—10%; $K_2O$—2%; $MgO.Al_2O_3$ support—88% (surface area of 30 m²/g).

C. $MoO_3$—1%; $K_2O$—2%; Graphite support—97% (manufactured by Union Carbide Co. as BB-6 with a surface area of 1–5 m²/g).

D. $MoO_3$—30%; $K_2O$—4%; Silica support—66% (manufactured by Johns-Manville Products as Celite-410, analyzed as $SiO_2$—86%; $Al_2O_3$—9%; CaO—1%; $Fe_2O_3$—2%; Misc.—2%; with a surface area of 3 m²/g).

| Process parameters: | A | B | C | D |
|---|---|---|---|---|
| Temperature (°C.) | 420 | 407 | 420 | 366 |
| Pressure (psig) | 300 | 300 | 300 | 300 |
| HSV (hr$^{-1}$) | 291 | 474 | 330 | 325 |
| $H_2$:CO (mole quotient) | 0.75 | 1.1 | 0.78 | 0.78 |

| | Selectivity (Carbon mole %) | | | |
|---|---|---|---|---|
| Process Results: | A | B | C | D |
| Paraffins | | | | |
| $C_1$ | 22.2 | 24.2 | 21.4 | 29 |
| $C_2$ | 3.7 | 6.4 | 5 | 26 |
| $C_3$ | 2.6 | 5.2 | 2 | 10 |
| $C_4$ | 1.1 | 0.7 | — | 4.3 |
| Olefins | | | | |
| $C_2$ | 9.3 | 8.9 | 14 | 3.7 |
| $C_3$ | 7.3 | 12.1 | 12.3 | 11.7 |
| $C_4$ | 2.9 | 6.6 | 4.6 | 6.8 |
| Paraffins and Olefins | | | | |
| $C_5$ plus | 50.9 | 34.5 | 40.5 | 8.5 |
| CO Conversion (%) | 25 | 55 | 26 | 49 |

Although the invention has been described in considerable detail, it must be understood that such detail is for the purpose of illustration only and that many variations and modifications can be made by one skilled in the art without departing from the spirit and scope of the invention.

What is claimed is:

1. In a process for producing hydrocarbons by contacting carbon monoxide and hydrogen at reactive conditions, the improvement which comprises increasing the yield of olefinic hydrocarbons containing from two to four carbon atoms by contacting the carbon monoxide and hydrogen with a catalyst having a surface area less than about 100 m²/g and consisting essentially of:
   (A) between about 1 percent and about 95 percent by weight based upon the weight of the catalyst of at least one material selected from the group consisting of the sulfide, oxide or metal of molybdenum, tungsten, rhenium, ruthenium, nickel, palladium, rhodium, osmium, iridium and platinum; and
   (B) between about 0.05 percent and about 50 percent by weight based upon the weight of the catalyst of at least one material selected from the group consisting of the hydroxide, oxide or salt of lithium, sodium, potassium, rubidium, cesium, magnesium, calcium, strontium, barium and thorium.

2. The process of claim 1 wherein the catalyst has a surface area less than about 40 m²/g.

3. The process of claim 2 wherein the catalyst consists essentially of, in addition to A and B, between about 1 and about 98.95 percent by weight based upon the weight of the catalyst of a support.

4. The process of claim 3 wherein the support is alumina, carbon, silica, zirconia, zircon, magnesia, titanium dioxide or mixtures thereof.

5. The process of claim 3 wherein the support is alumina.

6. The process of claim 3 wherein B is at least one material selected from the group consisting of the hydroxide, oxide or salt of lithium, sodium, potassium, rubidium or cesium.

7. The process of claim 3 wherein B is at least one material selected from the group consisting of the hydroxide, oxide or salt of potassium.

8. The process of claim 3 wherein A is at least one material selected from the group consisting of the sulfide, oxide or metal of molybdenum or tungsten.

9. The process of claim 3 wherein A is at least one material selected from the group consisting of the sulfide, oxide or metal of molybdenum.

10. The process of claim 8 wherein B is at least one material selected from the group consisting of the hydroxide, oxide or salt of lithium, sodium, potassium, rubidium or cesium.

11. The process of claim 10 wherein the support is alumina, carbon, silica, zirconia, zircon, magnesia, titanium dioxide or mixtures thereof.

12. The process of claim 11 wherein A is at least one material selected from the group consisting of the sulfide, oxide or metal of molybdenum.

13. The process of claim 12 wherein B is at least one material selected from the group consisting of the hydroxide, oxide or salt of potassium.

14. The process of claim 13 wherein the support is alumina.

15. The process of claim 3 wherein the catalyst consists essentially of between about 10 and about 50 percent A.

16. The process of claim 15 wherein the catalyst consists essentially of between about 1 and about 10 percent B.

17. The process of claim 16 wherein the catalyst consists essentially of at least about 40 percent of the support.

18. The process of claim 16 wherein the catalyst consists essentially of at least about 60 percent of the support.

19. The process of claim 18 wherein the support is alumina, carbon, silica, zirconia, zircon, magnesia, titanium dioxide or mixtures thereof.

20. The process of claim 18 wherein the support is alumina.

21. The process of claim 18 wherein B is at least one material selected from the group consisting of the hydroxide, oxide or salt of lithium, sodium, potassium rubidium or cesium.

22. The process of claim 18 wherein B is at least one material selected from the group consisting of the hydroxide, oxide or salt of potassium.

23. The process of claim 18 wherein A is at least one material selected from the group consisting of the sulfide, oxide or metal of molybdenum and tungsten.

24. The process of claim 18 wherein A is at least one material selected from the group consisting of the sulfide, oxide or metal of molybdenum.

25. The process of claim 23 wherein B is at least one material selected from the group consisting of the hydroxide, oxide or salt of lithium, sodium, potassium, rubidium and cesium.

26. The process of claim 25 wherein the support is alumina, silica, carbon, zirconia, zircon, magnesia, titanium dioxide or mixtures thereof.

27. The process of claim 26 wherein A is a sulfide, oxide or metal of molybdenum.

28. The process of claim 27 wherein B is a hydroxide, oxide or salt of potassium.

29. The process of claim 28 wherein the support is alumina.